(12) United States Patent
Kawarai

(10) Patent No.: US 11,224,756 B2
(45) Date of Patent: Jan. 18, 2022

(54) MAGNETIC FIELD GENERATING-APPARATUS FOR BIOSTIMULATION

(71) Applicant: SUMIDA CORPORATION, Tokyo (JP)

(72) Inventor: Mitsugu Kawarai, Natori (JP)

(73) Assignee: SUMIDA CORPORATION, Tokyo (JP)

(*) Notice: Subject to any disclaimer, the term of this patent is extended or adjusted under 35 U.S.C. 154(b) by 183 days.

(21) Appl. No.: 16/565,991

(22) Filed: Sep. 10, 2019

(65) Prior Publication Data
US 2020/0101309 A1   Apr. 2, 2020

(30) Foreign Application Priority Data
Sep. 27, 2018  (JP) .............................. JP2018-182673

(51) Int. Cl.
*A61N 2/00*   (2006.01)
*H01F 7/20*   (2006.01)
(Continued)

(52) U.S. Cl.
CPC .............. *A61N 2/006* (2013.01); *A61N 2/02* (2013.01); *H01F 7/20* (2013.01); *H01F 27/24* (2013.01); *H01F 27/28* (2013.01)

(58) Field of Classification Search
CPC .. A61N 2/006; A61N 2/02; H01F 7/20; H01F 27/24; H01F 27/28; H01F 7/202;
(Continued)

(56) References Cited

U.S. PATENT DOCUMENTS

| 3,658,051 A | * | 4/1972 | MacLean | ................. A61N 2/02 |
| | | | | 600/14 |
| 4,359,706 A | * | 11/1982 | Flack | ........................ H01F 7/00 |
| | | | | 335/281 |

(Continued)

FOREIGN PATENT DOCUMENTS

| DE | 2707574 A1 | 8/1978 |
| EP | 0143453 A2 | 6/1985 |

(Continued)

OTHER PUBLICATIONS

Goetz SM, Deng ZD. The development and modelling of devices and paradigms for transcranial magnetic stimulation. International Review of Psychiatry (Abingdon, England). Apr. 2017;29(2):115-145. DOI: 10.1080/09540261.2017.1305949. (Year: 2017).*

(Continued)

*Primary Examiner* — Navin Natnithithadha
*Assistant Examiner* — Sunita Reddy
(74) *Attorney, Agent, or Firm* — Cantor Colburn LLP

(57) ABSTRACT

A magnetic field generating-apparatus for biostimulation including: a C-shaped annular core having a gap-portion; and coils wound around the core, wherein the core includes a pair of facing extended-portions which lie on the both sides of the gap-portion and which face each other by extending toward the adjacent directions, and includes a pair of opposite-side portions which are juxtaposed on the respective outsides of the pair of facing extended-portions, and wherein the coils are wound around the pair of opposite-side portions respectively.

5 Claims, 6 Drawing Sheets

(51) Int. Cl.
*H01F 27/24* (2006.01)
*H01F 27/28* (2006.01)
*A61N 2/02* (2006.01)

(58) Field of Classification Search
CPC .......... H01F 7/204; H01F 27/306; H01F 3/00; H01F 5/00
USPC ...................................................... 600/9–15
See application file for complete search history.

(56) References Cited

U.S. PATENT DOCUMENTS

| | | | | |
|---|---|---|---|---|
| 4,727,754 | A * | 3/1988 | Ruckel | G01F 1/586 600/504 |
| 4,985,678 | A * | 1/1991 | Gangarosa | G01R 33/3806 324/318 |
| 5,305,749 | A * | 4/1994 | Li | G01R 33/421 600/415 |
| 5,741,316 | A * | 4/1998 | Chen | A61N 1/3787 607/61 |
| 6,048,302 | A * | 4/2000 | Markoil | A61N 2/02 600/13 |
| 6,210,317 | B1 * | 4/2001 | Bonlie | A61N 2/02 600/9 |
| 6,500,110 | B1 * | 12/2002 | Davey | A61N 2/02 128/DIG. 25 |
| 6,527,694 | B1 * | 3/2003 | Ishikawa | A61N 2/006 600/9 |
| 9,072,891 | B1 * | 7/2015 | Rao | A61N 2/02 |
| 2006/0122454 | A1 * | 6/2006 | Riehl | A61N 2/008 600/9 |
| 2007/0027353 | A1 | 2/2007 | Ghiron et al. | |
| 2007/0260107 | A1 * | 11/2007 | Mishelevich | A61N 2/004 600/14 |
| 2011/0105826 | A1 * | 5/2011 | Mishelevich | A61N 2/006 600/13 |
| 2012/0296150 | A1 * | 11/2012 | Pletnev | A61N 5/0613 600/13 |
| 2013/0317281 | A1 * | 11/2013 | Schneider | A61N 2/008 600/13 |
| 2015/0273233 | A1 | 10/2015 | Andalib et al. | |

FOREIGN PATENT DOCUMENTS

| | | |
|---|---|---|
| FR | 2445151 A1 | 7/1980 |
| JP | H07171220 A | 7/1995 |
| JP | 08052231 A | 2/1996 |
| WO | 9616692 A1 | 6/1996 |
| WO | 0002619 A2 | 1/2000 |

OTHER PUBLICATIONS

EPO Extended European Search Report for corresponding EP Application No. 19200054.5, dated Mar. 3, 2020.

* cited by examiner

<Prior Art>

MAGNETIC FIELD GENERATING-APPARATUS FOR BIOSTIMULATION

CROSS REFERENCES TO RELATED APPLICATIONS

The present invention contains subject manner related to Japanese Patent Application 2018-182673 filed in the Japanese Patent Office on Sep. 27, 2018, the entire contents of which being incorporated herein by reference.

BACKGROUND OF THE INVENTION

Field of the Invention

The present invention relates to a magnetic field generating-apparatus for biostimulation.

Description of the Related Art

As medical-use rehabilitation equipment used for such as dementia improvement or the like, there goes into circulation an AC magnetic field generating-apparatus which applies strong magnetic field to the inside of a living body. For such a magnetic field generating-apparatus, electricity is charged into a capacitor and is discharged through a semiconductor switch to a serially connected coil, in which by flowing an impulse-shaped electric current through the coil with an LC resonance frequency, there is generated an AC magnetic field. Then, there has been requested an apparatus which can operate stably and continuously even in a case in which a joule heat is generated when flowing an electric current through the coil.

For example, in a Patent Document 1 (Japanese unexamined patent publication No. H8-52231), there is disclosed, as a technology for suppressing the heat generation caused by the joule heat of the coil, a magnetic stimulation apparatus having a magnetic flux compression unit in which the winding diameter of the winding-wire becomes smaller gradually.

SUMMARY OF THE INVENTION

In addition, in a magnetic field generating-apparatus using an air-core coil, the maximum magnetic field is generated in the vicinity of the conductive wire which constitutes the coil, and in a magnetic field generating-apparatus using a magnetic-body core, it is generated in the vicinity of the core end-portion, in which it becomes that the magnetic field decreases rapidly as being away from its magnetic field forming unit.

On the other hand, for the transcranial magnetic stimulation, the target position, which is applied with the magnetic field, is in the inside of a skull-bone and lies in a deep portion of about 10 mm or more from the magnetic generating-apparatus applied to the head portion. In addition, also in case of a magnetic stimulation for rehabilitation of four limbs, the muscle tissue lies in a deep portion of several millimeters or more under the skin.

Therefore, in order to exert the effect caused by the magnetic stimulation with respect to the living body, it is necessary that a high magnetic field can be applied to a position apart from the magnetic field forming unit by around 10 mm.

The present invention was invented in view of the problem as mentioned above and is to provide a magnetic field generating-apparatus for biostimulation in which even under the condition that the power supply is made low in order to suppress the heat generation of the coil, it is possible to apply a high magnetic field to the target position at a deep portion of a living body.

According to the present invention, there is provided a magnetic field generating-apparatus for biostimulation including: a C-shaped annular core having a gap-portion; and coils wound around the core, wherein the core includes a pair of facing extended-portions which lie on the both sides of the gap-portion and which face each other by extending toward the adjacent directions, and includes a pair of opposite-side portions which are juxtaposed on the respective outsides of the pair of facing extended-portions, and wherein the coils are wound around the pair of opposite-side portions respectively.

According to the present invention, it is possible to provide a magnetic field generating-apparatus for biostimulation which can apply a high magnetic field to a target position at a deep portion of a living body even under the condition that the power supply is made low in order to suppress the heat generation of the coil.

DESCRIPTION OF THE PREFERRED EMBODIMENTS

Figure 1:
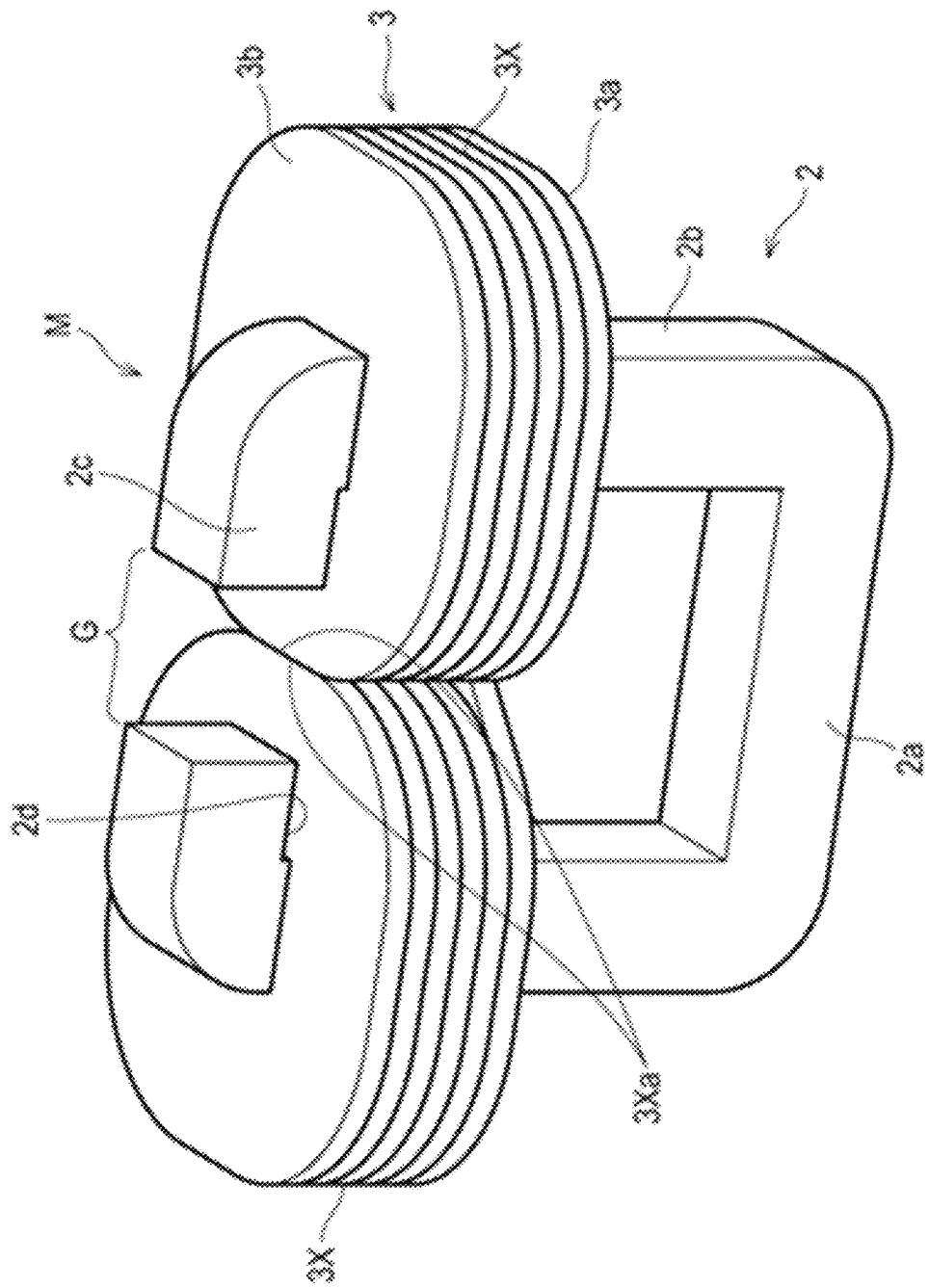
FIG. 1 is an upper-side perspective view of a magnetic field forming unit relating to an exemplified embodiment of the present invention.

Hereinafter, there will be explained exemplified embodiments of the present invention based on the drawings.

It should be noted that the exemplified embodiment explained hereinafter is only one example for making the understanding of the present invention easy and is not provided to limit the scope of the present invention. More specifically, with regard to the shape, the size, the arrangement and the like explained hereinafter, it is possible to change or improve them without departing from the gist of the present invention and also it is needless to say that the equivalents thereof will fall into the scope of the present invention.

In addition, in all the drawings, like reference numerals are applied to like constituents and repetitive explanations thereof will be appropriately omitted. In addition, in the present specification, there is a case in which the explanation is carried out by specifying the up and down directions, but this is to be set for convenience in order to explain the relative relation of the constituents and is not for limiting the directions when manufacturing or using the product relating to the present invention.

<<Outline>>

Figure 2:
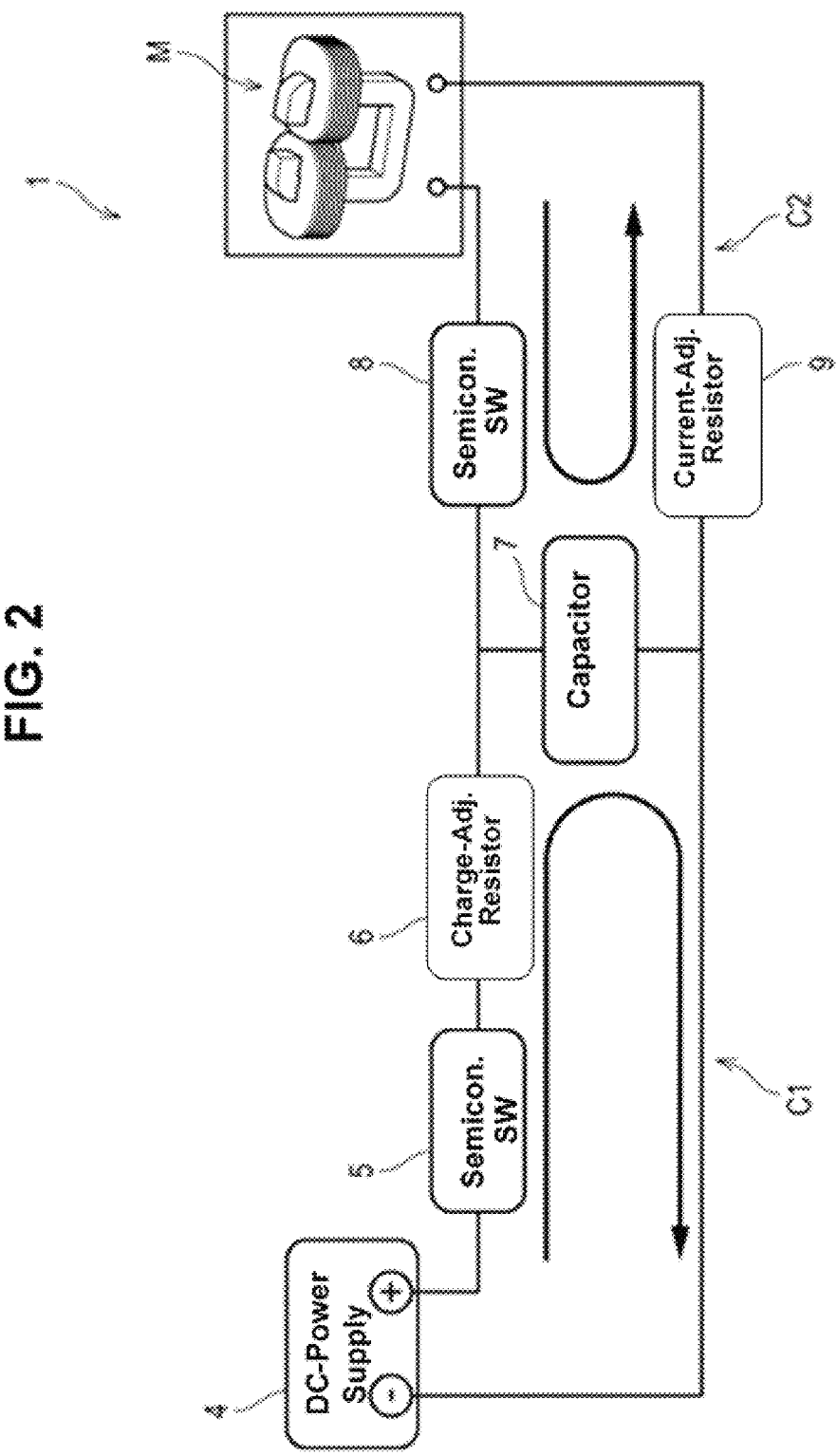
FIG. 2 is an explanatory diagram for explaining a constitution of a magnetic field generating-apparatus.

First, there will be explained the outline of a magnetic field forming unit M which is provided in a magnetic field generating-apparatus (magnetic field generating-apparatus for biostimulation) 1 relating to the present exemplified embodiment mainly with reference to FIG. 1 and FIG. 2. FIG. 1 is an upper-side perspective view of a magnetic field forming unit M relating to an exemplified embodiment of the present invention, and FIG. 2 is an explanatory diagram for explaining a constitution of a magnetic field generating-apparatus 1.

The magnetic field generating-apparatus for biostimulation (magnetic field generating-apparatus 1) relating to the exemplified embodiment of the present invention includes a C-shaped annular core 2 having a gap-portion G and coils 3 wound around the core 2.

The core 2 includes a pair of facing extended-portions 2c which lie on the both sides of the gap-portion G and which face each other by extending toward the adjacent directions, and includes a pair of opposite-side portions 2b which are juxtaposed on the respective outsides of the pair of facing extended-portions 2c.

It is characterized that the coils 3 are to be wound around the pair of opposite-side portions 2b respectively.

According to the abovementioned constitution, for the reason that the coils 3 are wound around the pair of opposite-side portions 2b, it becomes that the magnetic fluxes generated by the coils 3 toward the outward directions of the gap-portion G will be superimposed with the magnetic fluxes generated by the facing extended-portions 2c. Thus, it is possible to widen the flux distributions, which are generated by the core 2 and the coils 3, toward the outside of the gap-portion G, and it is possible to heighten the magnetic-flux density at a position (position apart by around 10 mm) which reaches a deep portion of a living body even under the condition that the power supply is made low in order to suppress the heat generation of the coil.

It should be noted that the abovementioned wording "C annular-shaped", as a whole, does not mean an arc-shaped object or a U-shaped object and means a shape, such as described above, which includes a pair of facing extended-portions 2c and a pair of opposite-side portions 2b and which includes portions in which the pair of facing extended-portions 2c and the pair of opposite-side portion 2b are connected by being crossed.

In addition, the abovementioned wording "by extending toward the adjacent directions" includes not only a configuration of being adjacent by extending along the same straight line but also a configuration of extending such that the extended lines thereof are inclined toward the directions to be crossed.

In addition, the abovementioned wording "facing" means "not directed toward the opposite sides" and includes not only a configuration in which mutually parallel surfaces face each other but also a configuration of facing each other by being inclined.

In addition, the wording "juxtaposed" means that they are provided on the both sides centering on the gap-portion G of the C-shaped annular coil 3 and other than a configuration of being provided linearly in parallel, there are included a configuration of being linearly provided by being inclined, a configuration of being provided by being curved and the like. Then, for the pair of opposite-side portions 2b, there is also included, for example, a configuration of being integrally formed without a boundary by being curved.

In addition, for the "gap-portion", an example of "air-gap" is shown, but it is allowed to constitute the "gap-portion" by a resin material or the like which has low magnetic-permeability compared with that of the core 2.

(The Whole Constitution)

There will be explained the constitution of the magnetic field generating-apparatus for biostimulation (magnetic field generating-apparatus 1) relating to the present exemplified embodiment mainly with reference to FIG. 2. The magnetic field generating-apparatus 1 is constituted by including a first circuit C1 connected with a DC-power supply 4 and a second circuit C2 connected with a magnetic field forming unit M.

For the first circuit C1, there are connected the DC-power supply 4, a semiconductor switch 5 which switches the on and off of the electric-conduction inside the circuit connected to the DC-power supply 4, an adjusting resistor 6 which adjusts the magnitude of the charging current and a charging capacitor 7.

The second circuit C2 is an LC circuit, in which there are connected the capacitor 7, a semiconductor switch 8 which switches the on and off of the electric-conduction inside the circuit connected to the capacitor 7 and an adjusting resistor 9 which adjusts the magnitude of the electric current supplied to the magnetic field forming unit M.

For an activating method of the magnetic field generating-apparatus 1, first, the semiconductor switch 5 is turned on and the capacitor 7 is charged by the first circuit C1 up to a specified voltage. If the charging to the capacitor 7 is completed, the semiconductor switch 5 is made to be "OFF".

Next, the semiconductor switch 8 is turned on and the electricity charged in the capacitor 7 is discharged through the coils 3 of the magnetic field forming unit M.

In the second circuit C2, an electric current of LC resonance flows repeatedly and magnetic fields are emitted from the coils 3 (from the magnetic field forming unit M). It should be noted that the semiconductor switches 5, 8 are controlled by a control circuit which is not shown.

(With Regard to Core)

Figure 3:
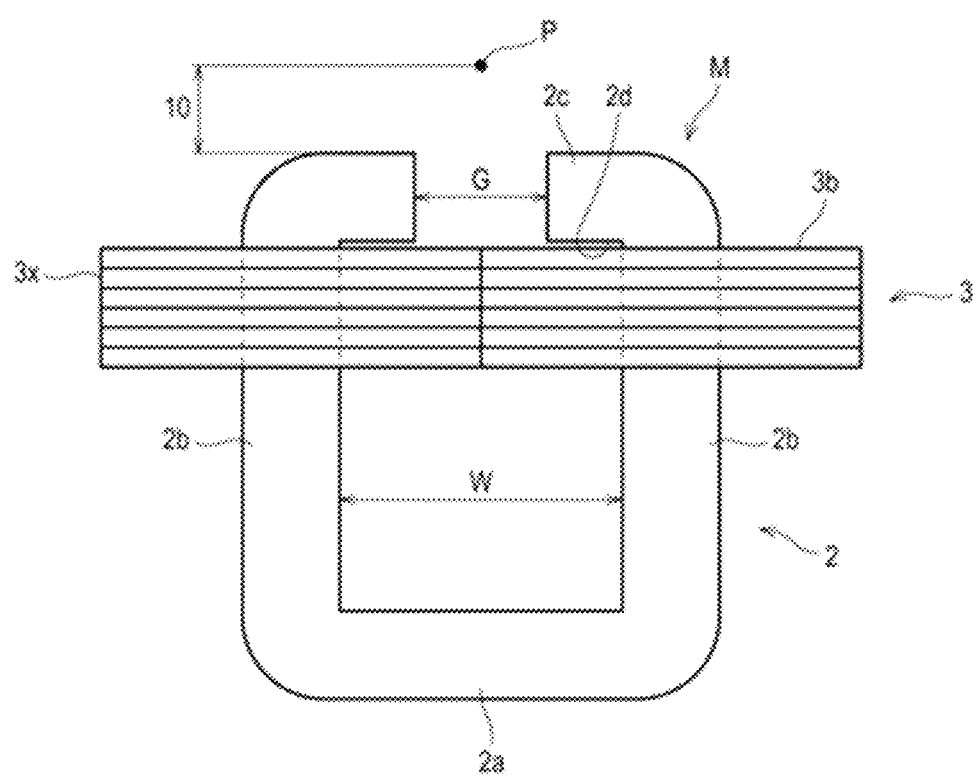
FIG. 3 is a front elevational view of a magnetic field forming unit and is an explanatory view for explaining an evaluation position of magnetic-flux density.
Figure 4:
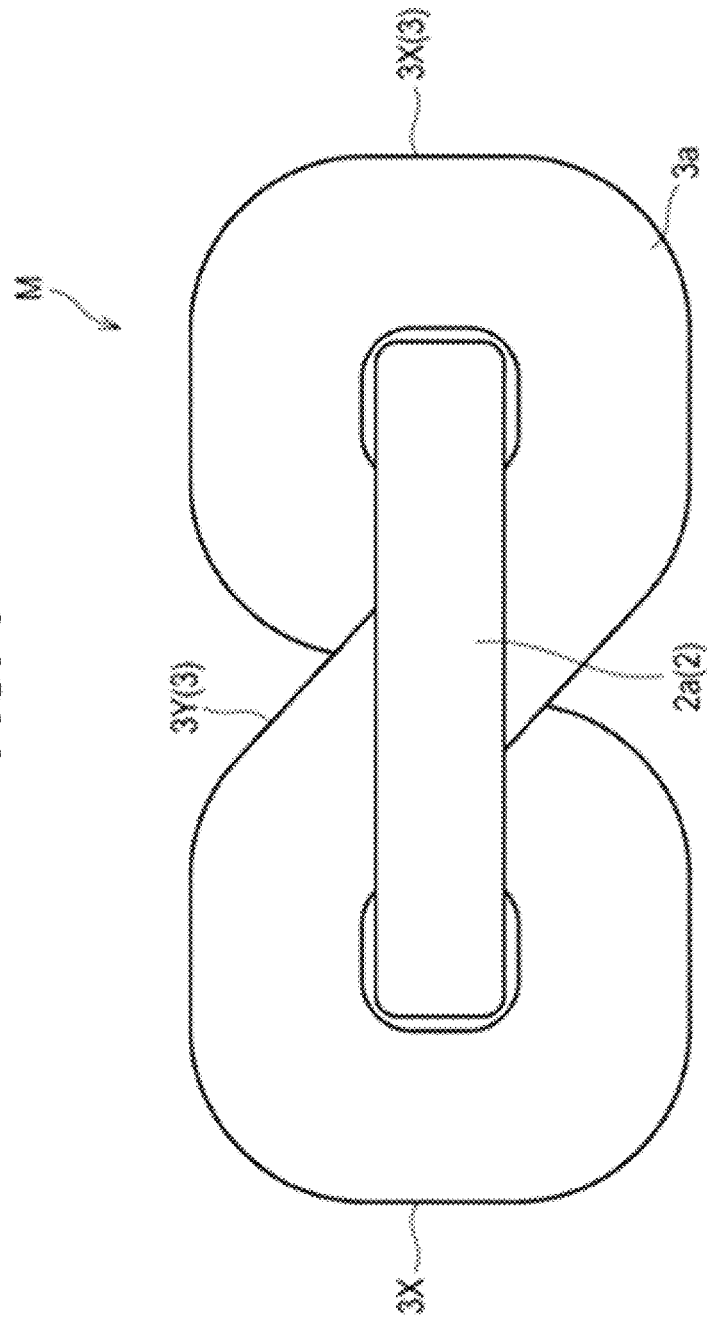
FIG. 4 is a bottom view of the magnetic field forming unit.

As shown in FIG. 1, FIG. 3 and FIG. 4, the core 2 is an object which guides the magnetic fluxes generated from the coils 3 to the gap-portion G and which generates magnetic fluxes at the gap-portion G.

FIG. 3 is a front elevational view of a magnetic field forming unit M and is an explanatory view for explaining an evaluation position P of the magnetic-flux density, and FIG. 4 is a bottom view of the magnetic field forming unit M.

The core 2 relating to the present exemplified embodiment is constituted by laminated electrical steel-sheets. As seen in FIG. 3, the core 2 is constituted by a pair of opposite-side portions 2b which extend in parallel toward the up and down direction, by a pair of facing extended-portions 2c which mutually extend toward adjacent directions within the lateral directions from the upper end-portions of the pair of opposite-side portions 2b and by a connecting portion 2a which mutually couples the lower end-portion of the pair of opposite-side portions 2b. In other words, the pair of facing extended-portions 2c extend toward the lateral directions which are orthogonal from the upper end-portions of the pair of opposite-side portions 2b which extend in the up and down direction. In addition, there is provided the gap-portion G between the pair of opposite-side portions 2b.

In the front view of FIG. 3, as one example, the external shape of the core 2 has 60 mm for vertical size and 50 mm for horizontal size, in which the width and the thickness relating to the cross section of the constitutional portion of the core 2 are 10 mm respectively. The magnetic-path length of this core 2 is, for example, 180 mm.

(With regard to Coils)

As one example, the pair of coils 3 are Edgewise-coils each of which is formed by an insulation-coated copper wire of a rectangular wire having a cross section of height "2 mm" and width "14 mm", in which the coils 3 have such winding-wire directions that the closed-loop directions of the magnetic-paths become the same and, as shown in FIG. 1 and FIG. 3, the coils 3 are wound around the opposite-side portions 2b of the core 2. The coils 3 are wound around the pair of opposite-side portions 2b respectively, as one example, by 6-turns for each and by 12-turns totally. Specifically, the end-portions (upper end-portions 3b) on the gap-portion G side for the coils 3 are wound around the opposite-side portions 2b respectively. In other words, it means that the upper end-portions 3b are not wound-around at the positions reaching the facing extended-portions 2c.

As shown in FIG. 1 and the like, the upper end-portions 3b relating to the present exemplified embodiment are not wound around the curved corner portions which are within the opposite-side portions 2b and which are the portions to be connected to the facing extended-portions 2c. However, it is allowed to employ a configuration in which the upper end-portions 3b are wound around the aforesaid corner portions and coils 3 are terminated.

According to the abovementioned constitution, by the magnetic fluxes which are generated from the upper end-portions 3b of the coils 3 wound around the opposite-side portions 2b, it is possible to heighten the magnetic-flux density at the outside of the gap-portion G of the core 2.

It should be noted that there is no limitation for the configuration in which the coils 3 are wound only around the opposite-side portions 2b and it is allowed to employ a configuration in which the coils 3 are wound around the connecting portion 2a and/or the facing extended-portions 2c in addition to the opposite-side portions 2b.

In particular, the end-portions (upper end-portions 3b) on the gap-portion G side for the coils 3 relating to the present exemplified embodiment are arranged in adjacent with the inside surfaces 2d of the facing extended-portions 2c.

Here, the wording "adjacent" means that the end-portion lies at the distance within a one-turn pitch of the winding-wire of the coil 3.

According to the abovementioned constitution, it becomes that the upper end-portions 3b of the coils 3 are arranged in adjacent with the gap-portion G and caused by the fringing effect, the magnetic fluxes will try to flow from the gap-portion G toward the coil 3 side, but it becomes that the spaces tried to be flown-into are to be buried by the upper end-portions 3b of the coils 3. For this reason, it becomes that the magnetic fluxes generated from the facing extended-portions 2c are induced by the upper end-portions 3b so as to flow toward the outside of the gap-portion G of the core 2.

Specifically in more detail, caused by the magnetic fluxes generated from the upper end-portions 3b of the coils 3, it is possible to induce the magnetic fluxes generated from the facing extended-portions 2c so as to be pushed-up toward the outside of the gap-portion G of the core 2. As a result thereof, it is possible to more heighten the magnetic-flux density at a position outwardly apart from the gap-portion G of the core 2 (at a position of a deep portion of a living body desired to be applied with the magnetic field) and by using lower electric-power, it is possible to apply an equivalent magnetic field as that in the past.

Further, it will be suitable if the upper end-portions 3b of the coils 3 are in close contact with the inside surfaces 2d.

According to such a constitution, it is possible to make the positional-alignment of the coils 3 easy by a configuration of abutting the coils to the inside surfaces 2d and as the movement of the coils 3 are restricted by the inside surfaces 2d, it becomes easy to maintain the positions thereof.

The coils 3 include spiral portions 3X at least two places and for the respective two places of spiral portions 3X, the side surfaces 3Xa of the two places of spiral portions 3X, which lie at the positions facing the gap-portion G, are in close contact with each other in a state of being wound around the pair of opposite-side portions 2b respectively.

Here, the wording "the side surfaces 3Xa of the two places of spiral portions 3X are in close contact with each other" is not limited by a configuration in which for the space between the respective wires (winding-wires), which mutually constitute the two places of spiral portions 3X, these side surfaces are completely in close contact with each other and there is also included a configuration in which at least one portion along the wire width (winding-wire width) thereof are in close contact with each other.

According to the abovementioned constitution, for the reason that the side surfaces 3Xa of the two places of spiral portions 3X in the coils 3 are in close contact with each other, it is possible to suppress a phenomenon that the magnetic fluxes, which are generated from the facing extended-portions 2c and pass through the gap-portion G, will leak toward the coils 3 side.

In addition, when the coils 3 are constituted by rectangular wires, it becomes easy for the side surfaces 3Xa of the two places of spiral portions 3X to closely contact with each other and therefore, this configuration is suitable, but there is no limitation by such a constitution and it is allowed to employ stranded wires having cross sections of circular shapes such as litz wires.

As seen in FIG. 4, the two places of spiral portions 3X are coupled by a coupling portion 3Y which extends linearly obliquely such that a front portion of one spiral portion 3X and a rear portion of the other spiral portion 3X are coupled at the lower end-portions 3a.

In this manner, the coils 3, which are constituted by the two places of spiral portions 3X and the coupling portion 3Y coupling those portions, are formed in a figure-8 shape shown by the bottom view of FIG. 4. In this manner, for the reason that the two places of spiral portions 3X are coupled by the coupling portion 3Y, it becomes that the two places of spiral portions 3X are wound in the winding-wire directions in which the closed-loop directions of their magnetic-paths are the same. By employing such a constitution, the closed-loop directions of the magnetic-paths become the same directions at the two places of spiral portions 3X and therefore, it becomes that it is easy for the magnetic fluxes to be concentrated and there can be obtained an excellent heat dissipation.

It should be noted that the two places of spiral portions 3X are not limited by a configuration of being coupled by the coupling portion 3Y and it is allowed to employ a configuration in which they are wound around the core 2 separately and there are provided separate input and output terminals.

As described above, if there is employed a configuration in which the two places of spiral portion 3X are coupled by the coupling portion 3Y and are formed in a figure-8 shape seen by the bottom view or there is employed a constitution in which the two places of spiral portions 3X are constituted separately, it is suitable in an aspect that it is easy for the side surfaces 3Xa of the two places of spiral portion 3X to be closely in contact with each other. However, the present invention is not to be limited by such constitutions.

For example, it is allowed to employ a configuration in which a single spiral-shaped coil originally constituted in a single form is arranged at the connecting portion 2a and thereafter, the coil is arranged separately from the center so as to be distributed toward the pair of opposite-side portions 2b. It is suitable for such a constitution not to use the Edgewise-coil but a coil constituted by a litz wire which is easily deformed and which has isotropy.

(With Regard to Gap)

Figure 5:
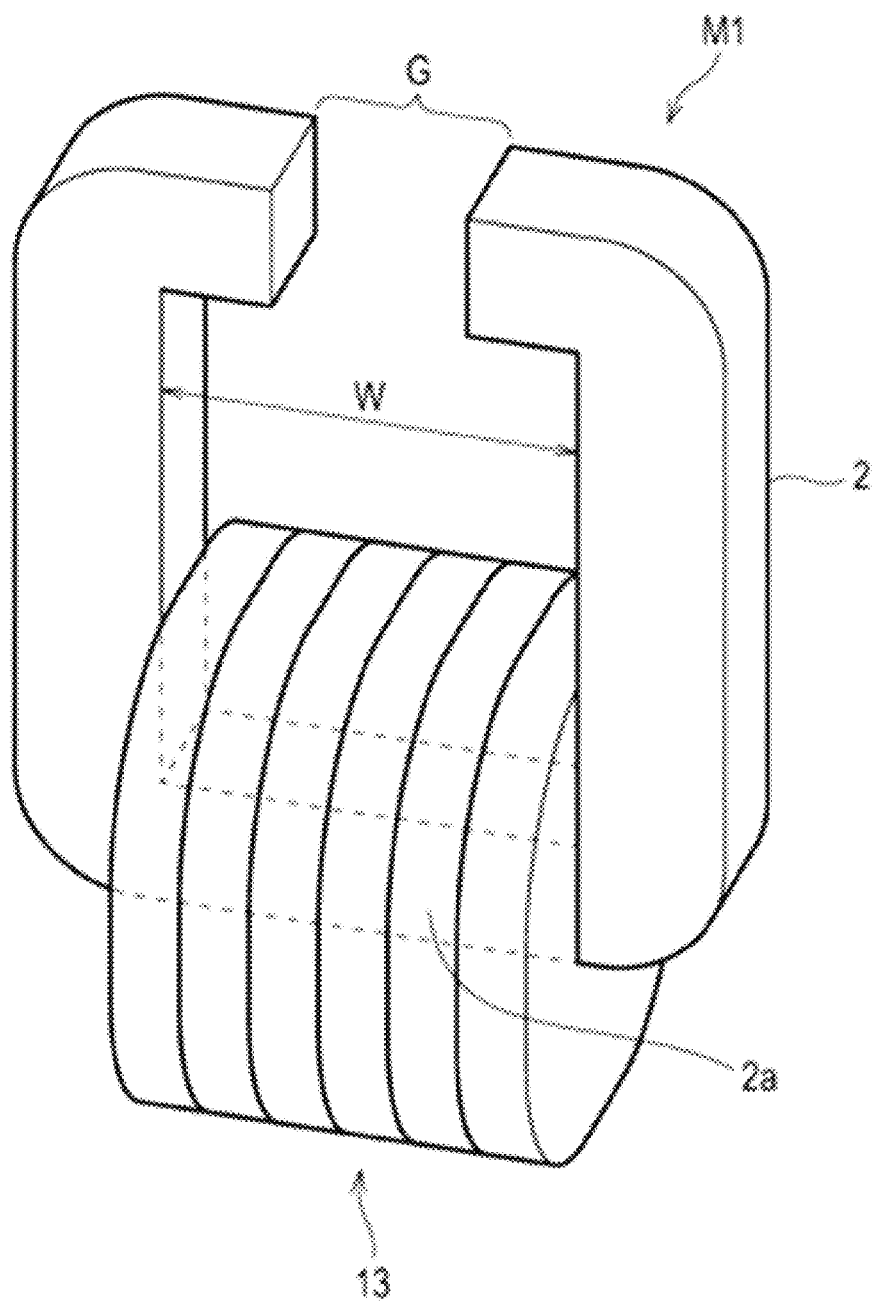
FIG. 5 is an upper-side perspective view showing a magnetic field forming unit which is a comparative example.

Next, there will be explained the relationship between the length of the gap-portion G and the magnetic-flux density at the evaluation position P and the relationship between the winding position of coils 3 (13) and the magnetic-flux density with reference to FIG. 5 and Table 1 in addition to FIG. 3 which shows the magnetic field forming unit M of an inventive example. FIG. 5 is an upper-side perspective view showing a magnetic field forming unit M1 of a comparative example.

It should be noted that the evaluation position P is a position which is 10 mm away from the outer periphery of the gap-portion G of the core 2 and which is supposed to be a position at a deep portion of a living body for which the AC magnetic field is generated.

For the present inventive example and the comparative example, there are used various kinds of cores 2 which have The magnetic field forming unit M1 relating to the comparative example is a unit which includes the coil 13 wound around the connecting portion 2a in the core 2.

The coil 13 as a comparative example is an insulation-coated copper wire having a cross section of height "6 mm" and width "4.7 mm", in which the coil is wound around the connecting portion 2a of the core 2 by 6-turns and by 12-turns totally for each of the inner layer and outer layer thereof.

The respective magnetic field forming units M, M1 have different lengths of the gap-portions G of the cores 2 and therefore, the inductance values thereof are different even if winding same number of turns for the coils 3, 13 respectively.

Then, it is necessary to obtain the same impulse-shaped alternating current even in case of employing either one of the magnetic field forming units M, M1 having different types of cores 2. With regard to the impulse width (frequency), the capacitance value of the capacitor 7 which is connected in series was appropriately adjusted such that the LC resonant frequency (which is 2 KHz in the present exemplified embodiment)

|  | Length (mm) of Gap-portion G | Length (mm) of Gap-portion G vs Distance W between Inner Edges | Length (mm) of Gap-portion G vs Magnetic-path Length | Magnetic-flux Density Ratio at "P" | Evaluation |
|---|---|---|---|---|---|
| Comparative Example 1 | 30 | 100% | 16.7% | 1 | — |
| Comparative Example 2 | 25 | 83.3% | 13.9% | 1.06 | X |
| Comparative Example 3 | 20 | 66.7% | 11.1% | 1.18 | X |
| Comparative Example 4 | 15 | 50.0% | 8.3% | 1.24 | X |
| Comparative Example 5 | 10 | 33.3% | 5.6% | 1.24 | X |
| Comparative Example 6 | 5 | 16.7% | 2.8% | 1.18 | X |
| Comparative Example 7 | 2 | 6.7% | 1.1% | 0.88 | X |
| Inventive Example 1 | 30 | 100% | 16.7% | 1.76 | Δ |
| Inventive Example 2 | 25 | 83.3% | 13.9% | 2.88 | ○ |
| Inventive Example 3 | 20 | 66.7% | 11.1% | 3.41 | ○ |
| Inventive Example 4 | 15 | 50.0% | 8.3% | 3.76 | ○ |
| Inventive Example 5 | 10 | 33.3% | 5.6% | 3.47 | ○ |
| Inventive Example 6 | 5 | 16.7% | 2.8% | 2.65 | ○ |
| Inventive Example 7 | 2 | 6.7% | 1.1% | 1.47 | Δ | different widths of the gap-portions G from maximum 30 mm to minimum 2 mm and there were carried out comparisons between the magnetic field forming unit M constituted by the coil 3 shown in FIG. 1 and the magnetic field forming unit M1 constituted by the coil 13 shown in FIG. 5.

As explained in the above description, each of the coils 13 as an inventive example is an insulation-coated copper wire having a cross section of height "2 mm" and width "14 mm", in which the coils are wound around the pair of opposite-side portions 2b respectively by 6-turns for each and by 12-turns totally such that portions of the coils face the gap-portion G.

becomes identical. The pulse width was set to be 0.5 msec.

In addition, the peak electric current (300 A in the present exemplified embodiment) flowing through the coil 3, 13 was adjusted by the charging voltage at the time of charging the capacitor 7 and by the adjusting resistor 9 which is inserted in series between the coil 3, 13 and the capacitor 7.

There is shown the results of the inventive examples in a table below. With regard to the magnetic-flux densities, the magnetic-flux density at the evaluation position P in case of a comparative example 1 is set as a reference value and the values of other comparative examples and of the inventive examples are indicated relatively. The magnetic-path length relating to the present exemplified embodiment is 180 mm such as mentioned above and the distance W between the inner edges, which is the facing distance between the inner edges of the pair of opposite-side portions 2b in the core 2, is 30 mm.

[Table 1]
<With Regard to Relationship Between Length of Gap-Portion G and Magnetic-Flux Density>

As understood from this result above, by setting the ratio of the length of the gap-portion G vs the distance W between the inner edges to be 6.7% or more and 100% or less and by forming the coils 3 in adjacent with the inside surfaces 2d of the core 2 such as seen in the inventive examples 1 to 7, there was a drastic improvement for the magnetic-flux density at the evaluation position P.

In other words, by setting the ratio of the length of the gap-portion G vs the magnetic-path length to be 1.1% or more and 16.7% or less and by forming the coils 3 in adjacent with the inside surfaces 2d of the core 2 such as seen in the inventive examples 1 to 7, there was a drastic improvement for the magnetic-flux density at the evaluation position P.

In a case in which the ratio of the length of the gap-portion G vs the distance W between the inner edges is 6.7% or more (in a case in which the ratio of the length of the gap-portion G vs the magnetic-path length is 1.1% or more, the gap does not become too narrow and the magnetic flux is efficiently induced outward the gap-portion G, and therefore, it is possible to heighten the magnetic flux at the evaluation position P.

In addition, in a case in which the ratio of the length of the gap-portion G vs the magnetic-path length is 16.7% or less, the gap does not become too wide and the generated magnetic fluxes are not few, and therefore, it is possible to heighten the magnetic flux of the evaluation position P.

In particular, it is suitable for the length gap-portion G to be 10% or more and 90% or less versus the distance W between the inner edges of the pair of opposite-side portions 2b. In other words, it is suitable for the core 2 relating to the present exemplified embodiment if the length of the gap-portion G thereof is set to be 2% or more and 15% or less versus the magnetic-path length.

In this manner, for the reason that the length of the gap-portion G is set to be 10% or more and 90% or less versus the distance W between the inner edges of the opposite-side portions 2b, it is possible to heighten the magnetic-flux density effectively at the evaluation position P (position reaching an internal tissue of a living body).

For example, for the constitution in which the pair of opposite-side portions are curved, inclined or the like, this distance W between the inner edges means the distance between the inner edges at the respective connecting portions (upper end-portions) of the pair of facing extended-portions 2c within the distance between the inner edges of the pair of opposite-side portions.

In the abovementioned exemplified embodiment, the explanation thereof was carried out under the condition that only the lower end-portions 3a of the coils 3 are formed in a figure-8 shape, but the present invention is not limited by such a constitution. For example, it is allowed to employ such a constitution that the coils 3 are formed in a figure-8 shape having two holes as a whole in which the pair of opposite-side portions 2b will pass through those two holes respectively.

According to the abovementioned constitution, for the reason that the coils 3 are formed in a figure-8 shape, the coil can be extended inside the gap-portion G by crossing compared with the constitution of the two spiral shaped (annular) coils aligned therein and therefore, it is possible to suppress the magnetic flux passing the gap-portion G from leaking toward the coils 3 side.

<Modified Example>

In the abovementioned exemplified embodiment, the explanation thereof was carried out under the condition that the pair of facing extended-portions 2c are extended in the orthogonal direction from the upper end-portions of the pair of opposite-side portions 2b. Then, the explanation thereof was carried out under the condition that the coils 3 are arranged in adjacent with the inside surfaces 2d of the facing extended-portions 2c.

According to such a constitution, it is possible to suppress a phenomenon that the magnetic fluxes generated from the facing extended-portions 2c are headed inward the gap-portion G by the upper end-portions 3b of the coils 3 arranged in adjacent with the inside surfaces 2d of the facing extended-portion 2c. However, the present invention is not limited by such a constitution.

Figure 6:
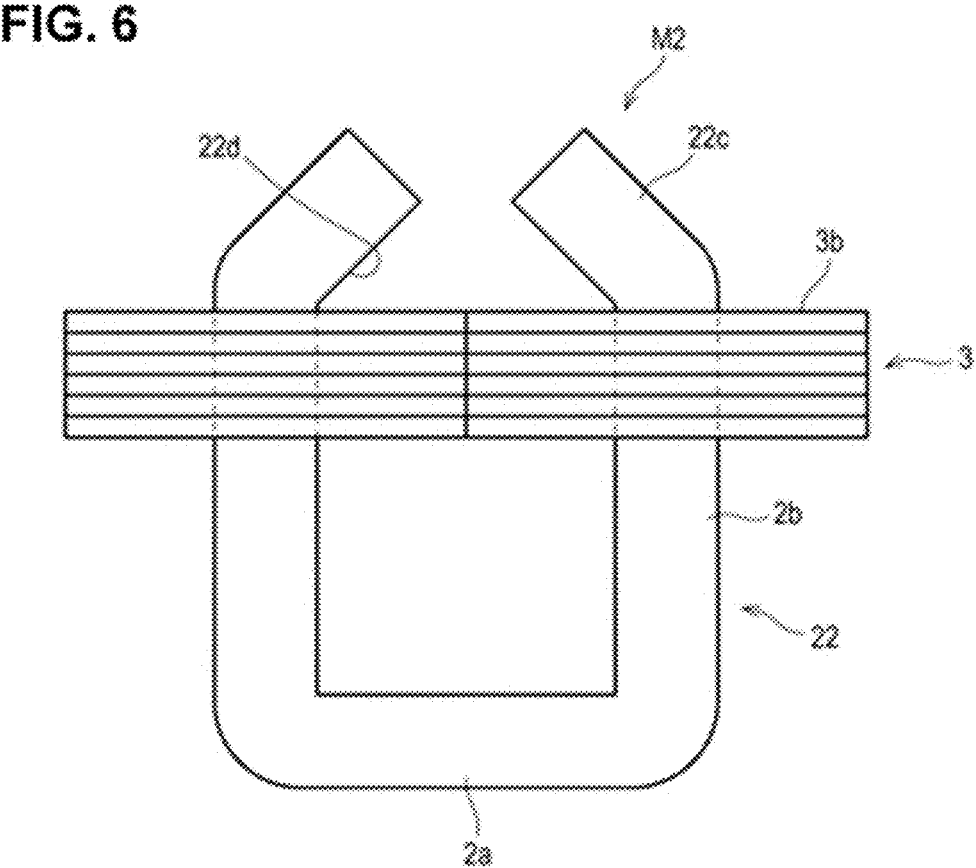
FIG. 6 is a front elevational view showing a magnetic field forming unit relating to a modified example.

Next, there will be explained a magnetic field forming unit M2 relating to a modified example with reference to FIG. 6. FIG. 6 is a front elevational view showing a magnetic field forming unit M2 relating to a modified example.

A core 22 constituting the magnetic field forming unit M2 includes facing extended-portions 22c which extend so as to be in adjacent with each other while being inclined upward from the upper end-portions of the pair of opposite-side portions 2b.

The coils 3 are fixed at the upper end-portions of the opposite-side portions 2b and there is provided spaces between the inside surfaces 22d of the facing extended-portions 22c and the coils 3.

Even if employing such a constitution, owing to the fact that the facing extended-portions 22c are inclined upward and that the magnetic fluxes emitted from the facing extended-portions 22c can be made directed outward (upward) the facing extended-portions 22c, it is possible to heighten the magnetic-flux density at a deep position of a living body. Further, the upper end-portions 3b of the coils 3 are directed upward and therefore, caused by the magnetic fluxes generated from the upper end-portion 3b of the coils 3, it is possible to prevent the magnetic fluxes generated from the facing extended-portions 22c from flowing toward the inside of the core 22.

The abovementioned each exemplified embodiment includes any one of the following technical ideas.

(1) A magnetic field generating-apparatus for biostimulation including:
   a C-shaped annular core having a gap-portion; and
   coils wound around the core,
   wherein the core includes a pair of facing extended-portions which lie on the both sides of the gap-portion and which face each other by extending toward the adjacent directions, and includes a pair of opposite-side portions which are juxtaposed on the respective outsides of the pair of facing extended-portions, and
   wherein the coils are wound around the pair of opposite-side portions respectively.

(2) The magnetic field generating-apparatus for biostimulation according to the item (1), wherein the end-portions on the gap-portion side for the coils are wound around the opposite-side portions.

(3) The magnetic field generating-apparatus for biostimulation according to the item (2), wherein the end-portions on the gap-portion side for the coils are arranged in adjacent with the inside surfaces of the facing extended-portions.

(4) The magnetic field generating-apparatus for biostimulation according to the item (3), wherein
the coils have spiral portions at least at two places, and for the respective two places of spiral portions, the side surfaces thereof at the two places of spiral portions which lie at the positions facing to the gap-portion are in close contact with each other, in a state of being wound around the respective pair of opposite-side portions.

(5) The magnetic field generating-apparatus for biostimulation according to the item (3), wherein
the coils are formed in a figure-8 shape including two holes, and the pair of opposite-side portions are passed through the two holes respectively.

(6) The magnetic field generating-apparatus for biostimulation according to any one of the items (1) to (5), wherein the length of the gap-portion is 10% or more and 90% or less with respect to the distance between the inner edges of the pair of opposite-side portions.

Having described preferred embodiments of the invention with reference to the accompanying drawings, it is to be understood that the invention is not limited to those precise embodiments and that various changes and modifications could be effected therein by one skilled in the art without departing from the spirit or scope of the invention as defined in the appended claims.

What is claimed is:

1. A magnetic field generating-apparatus for biostimulation comprising a magnetic field generating unit which comprises:
   a U-shaped annular core having two side portions opposite to and parallel with each other, wherein each side portion has a distal end; and
   coils having windings wound around the core, wherein
   the U-shaped core has a pair of extended-portions extending from the respective distal end of the two side portions and facing each other such that the pair of extended portions forms a gap-portion (G) therebetween,
   a length ratio between the gap-portion (G), a total magnetic path in the U-shaped core and the gap-portion (G), is not less than 1.1% and not more than 13.9%,
   the length of the gap-portion is 6.7% or more and 83.3% or less with respect to the distance between inner edges of the pair of opposite-side portions,
   a ratio comparing a first magnetic flux density at a position 10 mm away from an outer periphery of the gap-portion (G), and a second magnetic flux at a second position 10 mm away from a second outer periphery of a second gap-portion (G) of another sample, is not less than 1.47;
   wherein in the another sample, which includes a second U-shaped core consisting of a first arm, a second arm and a third arm, only one coil wound on the second arm of the second core, and a second gap-portion formed between the first arm and the third arm, and
   a ration between a length of the second gap-portion, and a second total magnetic path in the second U-shaped core and the second gap-portion is 16.7%.

2. The magnetic field generating-apparatus for biostimulation according to claim 1, wherein end-portions of the coils on a gap-portion side are wound around the opposite-side portions.

3. The magnetic field generating-apparatus for biostimulation according to claim 2, wherein the end-portions of the coils on the gap-portion side are arranged adjacently with inside surfaces of the facing extended-portions.

4. The magnetic field generating-apparatus for biostimulation according to claim 3, wherein
   the coils have spiral portions at least at two places, and
   for the respective two places of spiral portions, side surfaces thereof at the two places of spiral portions which lie at the positions facing the gap-portion are in close contact with each other, in a state of being wound around the respective pair of opposite-side portions.

5. The magnetic field generating-apparatus for biostimulation according to claim 3, wherein
   the coils are formed in a figure-8 shape including two holes, and
   the pair of opposite-side portions are passed through the two holes respectively.

* * * * *